United States Patent [19]

Fischer et al.

[11] Patent Number: 5,496,958
[45] Date of Patent: Mar. 5, 1996

[54] PREPARATION OF 5-VINYLPYRROLIDONES

[75] Inventors: Rolf Fischer, Heidelberg; Werner Hoffmann, Neuhofen; Ernst Langguth, Kirchheim; Hardo Siegel, Speyer, all of Germany

[73] Assignee: BASF Aktiengesellschaft, Ludwigshafen, Germany

[21] Appl. No.: 266,141

[22] Filed: Jun. 27, 1994

[30] Foreign Application Priority Data

Jul. 1, 1993 [DE] Germany ................ 43 21 870.9

[51] Int. Cl.[6] ................................ C07D 207/26
[52] U.S. Cl. ................................ 548/552; 548/543
[58] Field of Search ........................ 548/552, 543

[56] References Cited

U.S. PATENT DOCUMENTS 3,775,431 11/1973 Rodewald, Jr. ............ 260/326.5 F
5,286,875 2/1994 Fischer ..................... 548/547

FOREIGN PATENT DOCUMENTS 4038626 6/1991 Germany .

OTHER PUBLICATIONS

Janowitz et al, Synlett, No. 1 (1989) pp. 24–25.
Zalinyan et al, ". . . Stereoselective synthesis of ν–lactones," Chem. Abstracts, vol. 75, No. 3, 20181m (1971).

Primary Examiner—David B. Springer
Attorney, Agent, or Firm—John H. Shurtleff

[57] ABSTRACT

A process for the preparation of a 5-vinylpyrrolidone of the formula

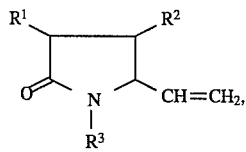

wherein each of $R^1$ and $R^2$ is hydrogen or alkyl and $R^3$ is preferably hydrogen but may further represent alkyl, cycloalkyl, aryl, alkylaryl, arylalkyl or a 5- to 6-membered aromatic or non-aromatic heterocyclic group containing 1 to 3 nitrogen atoms and/or an oxygen or sulfur atom, the process being carried out in two steps, first to react a 3-formylpropionic acid ester of the formula

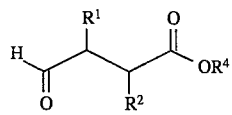

where each of $R^1$ and $R^2$ is hydrogen or $C_1$–$C_8$-alkyl, and $R^4$ is hydrogen, alkyl, cycloalkyl, aryl, alkylaryl or arylalkyl, with a vinylymagnesium halide of the formula $$CH_2=CH-Mg-X \qquad V,$$

where X is chlorine, bromine or iodine, at a temperature of from −30° to 100° C., under a pressure from 0.001 to 10 bar and in a molar ratio of V:IV of from 0.3:1 to 3:1 to obtain as an intermediate product a gamma-vinylbutyrolactone of the formula

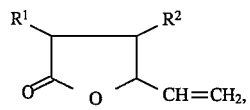

where $R^1$ and $R^2$ have the abovementioned meaning; and then reacting said intermediate of the formula II with ammonia or a primary amine of the formula $$R^3-NH_2 \qquad III,$$

where $R^3$ has the abovementioned meaning, at a temperature of from 150° to 350° C. and under a pressure of from 0.1 to 200 bar.

6 Claims, No Drawings

PREPARATION OF 5-VINYLPYRROLIDONES

The present application relates to a process for preparing 5-vinylpyrrolidones by reacting gamma-vinylbutyrolactones with ammonia or primary amines at elevated temperatures and to the preparation of the gamma-vinylbutyrolactones used as starting compounds by reacting 3-formylpropionic esters with vinylmagnesium halides.

DE-A 21 59 859 (U.S. Pat. No. 3,775,431) discloses that gamma-butyrolactam can be prepared by reacting gamma-butyrolactone and ammonia at elevated temperatures (200°–300° C.) and pressures (about 34 atm=500 psig). However, it is not possible to prepare gamma-lactams substituted in the gamma position from the corresponding lactones under the same conditions. Furthermore, DE-A 21 59 859 discloses that gamma-substituted (alkyl, alkenyl groups etc.) gamma-butyrolactones can be reacted with ammonia or primary amines at 200°–500° C. in the presence of crystalline alumosilicates to give corresponding 5-substituted pyrrolidones.

These procedures are unsatisfactory.

It is an object of the present invention to remedy the abovementioned disadvantages.

We have found that this object is achieved by a novel and improved process for preparing 5-vinylpyrrolidones of the general formula I

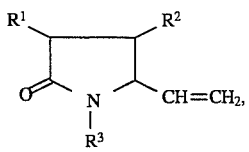

where $R^1$ and $R^2$ are hydrogen or $C_1$–$C_8$-alkyl, and $R^3$ is hydrogen, $C_1$–$C_{20}$-alkyl, $C_3$–$C_8$-cycloalkyl, aryl, $C_7$–$C_{12}$-alkylaryl, $C_7$–$C_{12}$-aralkyl or a heterocyclic radical, which comprises reacting gamma-vinylbutyrolactones of the general formula II

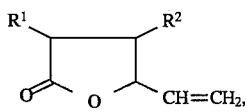

where $R^1$ and $R^2$ have the abovementioned meanings, with ammonia or primary amines of the general formula III $$R^3\text{—}NH_2 \quad (III),$$

where $R^3$ has the abovementioned meaning, at from 150° to 350° C. under from 0.1 to 200 bar, as well as by the preparation of gamma-vinylbutyrolactones II by reacting 3-formylpropionic esters of the general formula IV

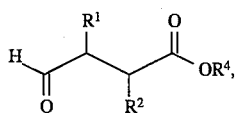

where $R^1$ and $R^2$ are hydrogen or $C_1$–$C_8$-alkyl, and $R^4$ is hydrogen, $C_1$–$C_{20}$-alkyl, $C_3$–$C_8$-cycloalkyl, aryl, $C_7$–$C_{12}$-alkylaryl or $C_7$–$C_{12}$-aralkyl, with vinylmagnesium halides of the general formula V $$CH_2=CH\text{—}Mg\text{—}X \quad (V),$$

where X is chlorine, bromine or iodine, at from −30° to 100° C. under from 0.001 to 10 bar in the molar ratio of V:IV of from 0.3:1 to 3:1.

The process according to the invention can be carried out as follows:

A mixture of gamma-vinylbutyrolactones (II) and ammonia or a primary amine (III) (with or without water and/or an inert solvent) can be reacted at from 150° to 350° C., preferably 200° to 320° C., particularly preferably 230° to 300° C., under from 0.1 to 200 bar, preferably 0.5 to 100 bar, particularly preferably 2 to 50 bar, in particular under the autogenous pressure of the system, batchwise or, preferably, continuously.

The holdup times are, as a rule, from 0.5 to 10 hours.

The reaction mixture can after cooling be worked up in a conventional way, e.g. by distillation.

Ammonia can be employed, for example, in anhydrous liquid form or else in aqueous form. Primary amines III can likewise be employed anhydrous or hydrous. The water content of the ammonia or of the primary amine III can, as a rule, be from 0 to 90% by weight, preferably 10 to 80% by weight, particularly preferably 20 to 70% by weight.

Examples of suitable inert solvents are aromatic compounds such as toluene or xylenes, hydrocarbons such as alkanes and cycloalkanes, ethers such as tetrahydrofuran or dioxane, or alcohols such as methanol, ethanol or the butanols.

Suitable primary amines III are aliphatic, aromatic, cycloaliphatic, araliphatic or heterocyclic primary amines. Examples of these are methylamine, n-octylamine, n-butylamine, cyclohexylamine, ethanolamine, benzylamine, cyclopentylamine and aniline.

The molar ratio of ammonia or the primary amine III to gamma-vinylbutyrolactones II is from 0.5:1 to 50:1, preferably 1:1 to 30:1, particularly preferably 2:1 to 20:1.

The gamma-vinylbutyrolactones II can be prepared according to the invention as follows:

A solution of a vinylmagnesium halide can be added to the 3-formylpropionic ester IV at from −30° to 100° C., preferably −10° to +20° C., under from 0.001 to 10 bar, preferably 0.1 to 3 bar, particularly preferably under atmospheric pressure, and then stirred at the reaction temperature and, where appropriate, at room temperature for, as a rule, from 0.5 to 2 hours. For workup, a dilute aqueous acid, but preferably water, can be added, and the precipitated magnesium salt can be removed, for example by filtration, and the filtrate can be worked up by distillation to isolate the gamma-vinylbutyrolactones II.

The reaction can be carried out batchwise or continuously. When it is carried out batchwise, it is possible in principle for the 3-formylpropionic ester IV to be added as such or dissolved in a solvent to the solution of the vinylmagnesium halide V. However, the reverse process is also possible.

It has proven particularly advantageous to add the vinylmagnesium halide solution to the 3-formylpropionic ester.

3-Formylpropionic esters IV can be prepared, for example, by hydroformylation of acrylic esters or derivatives thereof, in which a hydrogen atom in position 2 and/or 3 is replaced by alkyl radicals.

Examples of suitable 3-formylpropionic esters IV are methyl, ethyl, n-propyl, isopropyl, tert-butyl, n-butyl, pentyl, n-hexyl, dodecyl, cyclohexyl, cyclopentyl, cycloheptyl, phenyl, tolyl and benzyl esters.

The vinylmagnesium halides used, in particular vinylmagnesium chloride and bromide, can be prepared from vinyl chloride and bromide respectively and metallic magnesium in ethereal solvents, in particular tetrahydrofuran (Houben-Weyl, Methoden der organischen Chemie, 4th Edition, Volume 13, Part 2 a, pages 85 to 97 (1973)) and are also used in this form for the reaction according to the invention.

The molar ratio of vinylmagnesium halide V to 3-formylpropionic ester IV is, as a rule, from 0.3:1 to 3:1, preferably 0.5:1 to 1.5:1, particularly preferably 0.8:1 to 1.2:1.

Suitable and preferred solvents for the 3-formylpropionic esters IV are those in which the Grignard compound can also be prepared. However, it is also possible to employ two different solvents. Examples of solvents in which the 3-formylpropionic esters IV can be dissolved are cyclic and acyclic ethers such as tetrahydrofuran, diethyl ether, methyl tert-butyl ether and dioxane. Tetrahydrofuran is particularly preferred.

gamma-Vinylbutyrolactones II prepared by all processes disclosed in the literature can also be employed for the preparation according to the invention of 5-vinylpyrrolidones I.

The substituents $R^1$, $R^2$, $R^3$, $R^4$ and X in the compounds I, II, III, IV and V have the following meanings:

$R^1$, $R^2$, $R^3$ and $R^4$
independently of one another hydrogen, $R^1$ and $R^2$
- $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$–$C_4$-alkyl such as methyl, ethyl, n-propyl, isopropyl, n-butyl, isobutyl, sec-butyl and tert-butyl, particularly preferably methyl and ethyl, $R^3$ and $R^4$
- $C_1$–$C_{20}$-alkyl, preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, particularly preferably $C_1$–$C_4$-alkyl such as methyl, ethyl, n-propyl, isopropyl, n-butyl, isobutyl, sec-butyl and tert-butyl,
- $C_3$–$C_8$-cycloalkyl such as cyclopropyl, cyclobutyl, cyclopentyl, cyclohexyl, cycloheptyl and cyclooctyl, preferably cyclopentyl, cyclohexyl and cyclooctyl, particularly preferably cyclopentyl and cyclohexyl,
- aryl such as phenyl, 1-naphthyl, 2-naphthyl, 1-anthryl, 2-anthryl and 9-anthryl, preferably phenyl, 1-naphthyl and 2-naphthyl, particularly preferably phenyl,
- $C_7$–$C_{12}$-alkylaryl, preferably $C_7$–$C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl,
- $C_7$–$C_{12}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ additionally
- a heterocyclic, aromatic or non-aromatic radical such as five-membered heteroaromatics containing one to three nitrogen atoms and/or one oxygen or sulfur atom such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl or six-membered heteroaromatics containing one to three nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl or 5- to 6-membered, saturated or unsaturated heterocycles containing one to three nitrogen atoms and/or one oxygen or sulfur atom such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,1,2,4-triazolidin-3-yl, 1,3,4-oxadiazolidin-2-yl, 1,3,4-thiadiazolidin-2-yl, 1,3,4-triazolidin-2-yl, 2,3-dihydro-2-furyl, 2,3-dihydro-3-furyl, 2,4-dihydro-2-furyl, 2,4-dihydro-3-furyl, 2,3-dihydro-2-thienyl, 2,3-dihydro-3-thienyl, 2,4-dihydro-2-thienyl, 2,4-dihydro-3-thienyl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydro-1-pyrazolyl, 2,3-dihydro-2-pyrazolyl, 2,3-dihydro-3-pyrazolyl, 2,3-dihydro-4-pyrazolyl, 2,3-dihydro-5-pyrazolyl, 3,4-dihydro-1-pyrazolyl, 3,4-dihydro-3-pyrazolyl, 3,4-dihydro-4-pyrazolyl, 3,4-dihydro-5-pyrazolyl, 4,5-dihydro-1-pyrazolyl, 4,5-dihydro-3-pyrazolyl, 4,5-dihydro-4-pyrazolyl, 4,5-dihydro-5-pyrazolyl, 2,3-dihydro-2-oxazolyl, 2,3-dihydro-3-oxazolyl, 2,3-dihydro-4-oxazolyl, 2,3-dihydro-5-oxazolyl, 3,4-dihydro-2-oxazolyl, 3,4-dihydro-3-oxazolyl, 3,4-dihydro-4-oxazolyl, 3,4-dihydro-5-oxazolyl, 3,4-dihydro-2-oxazolyl, 3,4-dihydro-3-oxazolyl, 3,4-dihydro-4-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-2-triazinyl and 1,2,4-tetrahydro-3-triazinyl.

EXAMPLES

Example 1

840 ml of a 1.25 molar solution of vinylmagnesium chloride in tetrahydrofuran were added over the course of 30 minutes to 61 g (526 mmol) of methyl 3-formylpropionate in 500 ml of anhydrous tetrahydrofuran at 0°–5° C. with stirring. The mixture was then stirred at 0°–5° C. for one hour and subsequently at 20° C. for one hour. After addition of 105 g of water at 20° C., a crystalline precipitate separated out and was filtered off with suction and then washed twice with 100 ml of tetrahydrofuran each time. The combined filtrates were concentrated at 40° C./50 mbar. The residue was distilled using a spinning band column to result in 36.5 g (62%) of gamma-vinylbutyrolactone, boiling point 80° C./7.5 mbar.

Example 2

The reaction was carried out at −10° to −5° C. as in Example 1. The yield of gamma-vinylbutyrolactone after distillation was 52%.

Example 3

21 g (179 mmol) of gamma-vinylbutyrolactone prepared as in Example 1 were stirred with 100 ml of 25% strength aqueous ammonia in an autoclave at 270° C. for two hours. After cooling, the reaction mixture was concentrated at 50° C./20 mbar. The residue (19 g) was distilled using a spinning band column to yield 12.9 g (65%) of 5-vinylpyrrolidone, boiling point 88°–95° C./0.3 mbar.

Example 4

21 g (179 mmol) of gamma-vinylbutyrolactone prepared as in Example 1 were stirred with 125 g of 40% strength aqueous methylamine in an autoclave at 280° C. for two hours. After cooling, the reaction mixture was concentrated at 50° C./20 mbar. The residue (22.7 g) was distilled using a spinning band column to yield 10.3 g (46%) of 5-vinyl-N-methylpyrrolidone.

We claim:

1. A process for the preparation of a 5-vinylpyrrolidone of the formula

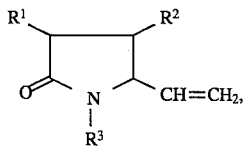

I wherein
each of $R^1$ and $R^2$ is hydrogen or $C_1$–$C_8$-alkyl, and $R^3$ is a substituent selected from the group consisting of hydrogen, $C_1$–$C_{20}$-alkyl, $C_3$–$C_8$-cycloalkyl, aryl, $C_7$–$C_{12}$-alkylaryl and $C_7$–$C_{12}$-arylalkyl,
said process comprising:
first reacting a 3-formylpropionic acid ester of the formula

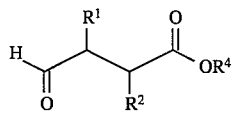

IV where
each of $R^1$ and $R^2$ is hydrogen or $C_1$–$C_8$-alkyl, and $R^4$ is a substituent selected from the group consisting of hydrogen, $C_1$–$C_{20}$-alkyl, $C_3$–$C_8$-cycloalkyl, aryl, $C_7$–$C_{12}$-alkylaryl and $C_7$–$C_{12}$-arylalkyl,
with a vinylmagnesium halide of the formula

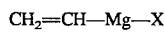

V, where X is chlorine, bromine or iodine, at a temperature of from −30° to 100° C., under a pressure from 0.001 to 10 bar and in a molar ratio of V:IV of from 0.3:1 to 3:1 to obtain as an intermediate product a gamma-vinylbutyrolactone of the formula

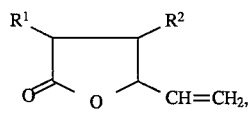

II where $R^1$ and $R^2$ have the abovementioned meaning; and then reacting said intermediate of the formula II with ammonia or a primary amine of the formula

III, where $R^3$ has the abovementioned meaning, at a temperature of from 150° to 350° C. and under a pressure of from 0.1 to 200 bar.

2. A process as claimed in claim 1, wherein the reaction of the intermediate II in the second step is carried out at a temperature of from 200° to 320° C. and under a pressure of from 0.5 to 100 bar.

3. A process as claimed in claim 1, wherein the reaction of the intermediate II in the second step is carried out under the autogenous pressure of the reaction mixture.

4. A process as claimed in claim 1, wherein the substituent $R^3$ is hydrogen in each of the formulas I and III.

5. A process as claimed in claim 4, wherein the reaction of the intermediate II in the second step is carried out at a temperature of from 200° to 320° C. and under a pressure of from 0.5 to 100 bar.

6. A process as claimed in claim 4, wherein the reaction of the intermediate II in the second step is carried out under the autogenous pressure of the reaction mixture.

* * * * *

UNITED STATES PATENT AND TRADEMARK OFFICE
CERTIFICATE OF CORRECTION

PATENT NO. : 5,496,958
DATED : March 5, 1996
INVENTOR(S) : Fischer et al.

It is certified that error appears in the above-identified patent and that said Letters Patent is hereby corrected as shown below:

IN THE CLAIMS:

Claim 1, Col. 6, line 1: cancel "firstreacting" and substitute --first reacting--.

Signed and Sealed this

Twentieth Day of August, 1996

Attest:

BRUCE LEHMAN

Attesting Officer     Commissioner of Patents and Trademarks